(12) United States Patent
Rocha-Singh et al.

(10) Patent No.: US 10,065,018 B2
(45) Date of Patent: Sep. 4, 2018

(54) APPARATUS AND METHOD FOR PROMOTING ANGIOGENESIS IN ISCHEMIC TISSUE

(71) Applicants: Krishna Rocha-Singh, Springfield, IL (US); Krishna Martinez-Singh, Albany, NY (US)

(72) Inventors: Krishna Rocha-Singh, Springfield, IL (US); Krishna Martinez-Singh, Albany, NY (US)

(*) Notice: Subject to any disclaimer, the term of this patent is extended or adjusted under 35 U.S.C. 154(b) by 20 days.

(21) Appl. No.: 15/268,069

(22) Filed: Sep. 16, 2016

(65) Prior Publication Data
US 2017/0266411 A1    Sep. 21, 2017

Related U.S. Application Data

(63) Continuation-in-part of application No. 15/072,249, filed on Mar. 16, 2016.

(51) Int. Cl.
*A61M 25/00* (2006.01)

(52) U.S. Cl.
CPC .... *A61M 25/0084* (2013.01); *A61M 25/0074* (2013.01); *A61M 2025/0092* (2013.01); *A61M 2205/32* (2013.01)

(58) Field of Classification Search
CPC . A61B 2018/0022; A61B 2018/00285; A61M 25/10; A61M 25/04;
(Continued)

(56) References Cited

U.S. PATENT DOCUMENTS 4,694,838 A  9/1987 Wijayarthna et al.
4,885,003 A  12/1989 Hillstead
(Continued)

FOREIGN PATENT DOCUMENTS

EP    1 587 440 A2   10/2005
EP    1 713 453 B1   10/2006
WO    WO-2012/166168 A1   12/2012

OTHER PUBLICATIONS

Asahara, et al., Bone Marrow Origin of Endothelial Progenitor Cells Responsible for Postnatal Vasculogensis in Physiological and Pathological Neovascularization, Circ. Res., 85:221-228 (1999).
(Continued)

*Primary Examiner* — Scott Medway
(74) *Attorney, Agent, or Firm* — Foley & Lardner LLP; Christopher C. Bolten; Nicola A. Pisano

(57) ABSTRACT

A biologics delivery device and method of use for promoting angiogenesis in occluded vessels and ischemic tissue of a patient are provided, wherein the biologics delivery device includes a catheter having a proximal end, a distal region having a distal end, and a side wall defining a catheter lumen; an expandable member disposed in the distal region, the expandable member configured to support a subintimal space in an occluded blood vessel of a patient, and to transition between a collapsed state and an expanded state; and a hollow needle having a penetration tip deployable from inside the catheter lumen to outside the catheter lumen, and into tissue surrounding the occluded blood vessel, wherein the expandable member in the expanded state allows the flow of oxygenated blood to the occluded blood vessel. Methods of using the inventive biologics delivery device also are provided to deposit the biologic from a subintimal space to tissue surrounding the occluded blood vessel.

9 Claims, 12 Drawing Sheets

(58) Field of Classification Search
CPC .... A61M 2025/105; A61M 2025/1052; A61M 2025/0681

See application file for complete search history.

(56) References Cited

U.S. PATENT DOCUMENTS

| | | | |
|---|---|---|---|
| 5,002,560 A | 3/1991 | MacHold et al. | |
| 5,034,001 A | 7/1991 | Garrison et al. | |
| 5,221,261 A | 6/1993 | Termin et al. | |
| 5,306,250 A * | 4/1994 | March | A61M 29/02 |
| | | | 604/104 |
| 5,383,856 A * | 1/1995 | Bersin | A61M 25/1002 |
| | | | 604/101.01 |
| 5,415,637 A | 5/1995 | Khosravi | |
| 5,449,372 A | 9/1995 | Schmaltz et al. | |
| 5,554,114 A | 9/1996 | Wallace et al. | |
| 5,603,694 A | 2/1997 | Brown et al. | |
| 5,653,689 A * | 8/1997 | Buelna | A61F 2/958 |
| | | | 604/103.09 |
| 5,713,860 A * | 2/1998 | Kaplan | A61B 8/12 |
| | | | 604/103.01 |
| 5,716,410 A | 2/1998 | Wang et al. | |
| 5,782,907 A | 7/1998 | Frantzen et al. | |
| 5,873,865 A | 2/1999 | Horzewski et al. | |
| 5,891,108 A | 4/1999 | Leone et al. | |
| 5,902,266 A | 5/1999 | Leone et al. | |
| 5,997,487 A | 12/1999 | Kolehmainen et al. | |
| 6,074,378 A | 6/2000 | Mouri et al. | |
| 6,090,115 A | 7/2000 | Beyar et al. | |
| 6,135,976 A | 10/2000 | Tachibana et al. | |
| 6,340,356 B1 | 1/2002 | Navia et al. | |
| 6,478,778 B1 | 11/2002 | Jacobsen et al. | |
| 6,635,027 B1 | 10/2003 | Cragg et al. | |
| 7,033,385 B2 | 4/2006 | Eder et al. | |
| 7,163,555 B2 | 1/2007 | Dinh | |
| 7,179,270 B2 | 2/2007 | Makower | |
| 7,824,704 B2 | 11/2010 | Anderson et al. | |
| 7,998,166 B2 | 8/2011 | Anderson et al. | |
| 8,257,383 B2 * | 9/2012 | Rottenberg | A61B 17/02 |
| | | | 606/194 |
| 8,585,713 B2 | 11/2013 | Ferrera et al. | |
| 8,608,661 B1 | 12/2013 | Mandrusov et al. | |
| 8,636,712 B2 | 1/2014 | Kugler et al. | |
| 8,647,311 B2 | 2/2014 | Dib | |
| 8,827,953 B2 | 9/2014 | Rocha-Singh | |
| 8,961,494 B2 | 2/2015 | Kugler et al. | |
| 8,998,841 B2 | 4/2015 | Shen et al. | |
| 8,998,936 B2 | 4/2015 | Alvarez et al. | |
| 2001/0000041 A1 | 3/2001 | Selmon et al. | |
| 2001/0007059 A1 * | 7/2001 | Mirzaee | A61M 25/0084 |
| | | | 604/164.03 |
| 2002/0032406 A1 | 3/2002 | Kusleika | |
| 2003/0171734 A1 * | 9/2003 | Seward | A61M 25/10 |
| | | | 604/506 |
| 2004/0015193 A1 * | 1/2004 | Lamson | A61N 1/056 |
| | | | 607/9 |
| 2004/0082962 A1 * | 4/2004 | Demarais | A61B 17/320725 |
| | | | 606/128 |
| 2004/0138562 A1 * | 7/2004 | Makower | A61M 25/0084 |
| | | | 600/439 |
| 2005/0171478 A1 * | 8/2005 | Selmon | A61B 17/3207 |
| | | | 604/164.01 |
| 2006/0106338 A1 * | 5/2006 | Chang | A61M 25/0084 |
| | | | 604/104 |
| 2006/0276749 A1 | 12/2006 | Selmon et al. | |
| 2007/0093779 A1 | 4/2007 | Kugler et al. | |
| 2007/0093781 A1 | 4/2007 | Kugler et al. | |
| 2008/0125748 A1 | 5/2008 | Patel | |
| 2008/0154172 A1 | 6/2008 | Mauch | |
| 2008/0200946 A1 * | 8/2008 | Braun | A61M 25/0054 |
| | | | 606/198 |
| 2008/0228171 A1 * | 9/2008 | Kugler | A61B 17/221 |
| | | | 604/529 |
| 2008/0243067 A1 | 10/2008 | Rottenberg et al. | |
| 2008/0249397 A1 | 10/2008 | Kapadia | |
| 2009/0076448 A1 * | 3/2009 | Consigny | A61B 17/22 |
| | | | 604/103.01 |
| 2009/0088685 A1 | 4/2009 | Kugler et al. | |
| 2009/0118700 A1 | 5/2009 | Callas et al. | |
| 2009/0124899 A1 | 5/2009 | Jacobs et al. | |
| 2009/0125053 A1 | 5/2009 | Ferrera et al. | |
| 2009/0264826 A1 | 10/2009 | Thompson | |
| 2009/0270906 A1 * | 10/2009 | Hossainy | A61F 2/82 |
| | | | 606/194 |
| 2009/0299171 A1 | 12/2009 | Duffy et al. | |
| 2010/0063534 A1 | 3/2010 | Kugler et al. | |
| 2010/0152682 A1 | 6/2010 | Mauch et al. | |
| 2011/0144677 A1 | 6/2011 | Ward et al. | |
| 2011/0264128 A1 | 10/2011 | Mauch et al. | |
| 2011/0295305 A1 | 12/2011 | Morero | |
| 2012/0265229 A1 | 10/2012 | Rottenberg et al. | |
| 2013/0072957 A1 | 3/2013 | Anderson | |
| 2013/0131594 A1 | 5/2013 | Bonnette et al. | |
| 2013/0317534 A1 | 11/2013 | Zhou et al. | |
| 2014/0180323 A1 | 6/2014 | Shriver | |
| 2014/0200504 A1 | 7/2014 | Rocha-Singh | |
| 2014/0277053 A1 | 9/2014 | Wang et al. | |
| 2015/0351782 A1 | 12/2015 | Kangas et al. | |

OTHER PUBLICATIONS

Behfar, et al., Optimized Delivery System Achieves Enhancement Endomyocardial Stem Cell Retention, Cir. Cardiovasc. Interv., 6(6):710-710 (2013).

Golomb, et al., Contemporary Reviews in Cardiovascular Medicine, Peripheral Arterial Disease, Morbidity and Mortality Implications, Circulation, 114:688-699 (2006).

Kurtz, A., Mesenchymal Stem Cell Delivery Routes and Fate, International Journal of Stem Cells, vol. 1, No. 1 (2008).

Li, et al., Identification of Pancreatic Cancer Stem Cells, Cancer Res., 67(3):1030-1037 (2007).

Luttun, et al., Vascular progenitors: from biology to treatment, Trends Cardiovasc. Med., 12(2):88-96 (2002).

Perin, et al., Comparison of intracoronary and transendocardial delivery of allogeneic mesenchymal cells in a canine model of acute myocardial infarction, J. Mol. Cell. Cardiol., 44(3):486-95 (2008).

Tateishi-Yuyama, et al., Therapeutic angiogenesis for patients with limb ischaemia by autologous transplantation of bone-marrow cells: a pilot study and a randomized controlled trial, Lancet, 360(9331):427-35 (2002).

Wang, et al., The Clinical Status of Stem Cell Therapy for Ischemic Cardiomyopathy, Hindawi Publishing Corporation, Stem Cells International, vol. 2015, Article ID 135023, 13 pages.

International Search Report & Written Opinion dated Aug. 9, 2017 in Int'l PCT Patent Application Serial No. PCT/US2017/022171.

Invitation to Pay Additional Fees & Communication Relating to the Results of the Partial International Search dated Jun. 19, 2017 in Int'l PCT Patent Appl Serial No. PCT/US17/022171.

* cited by examiner

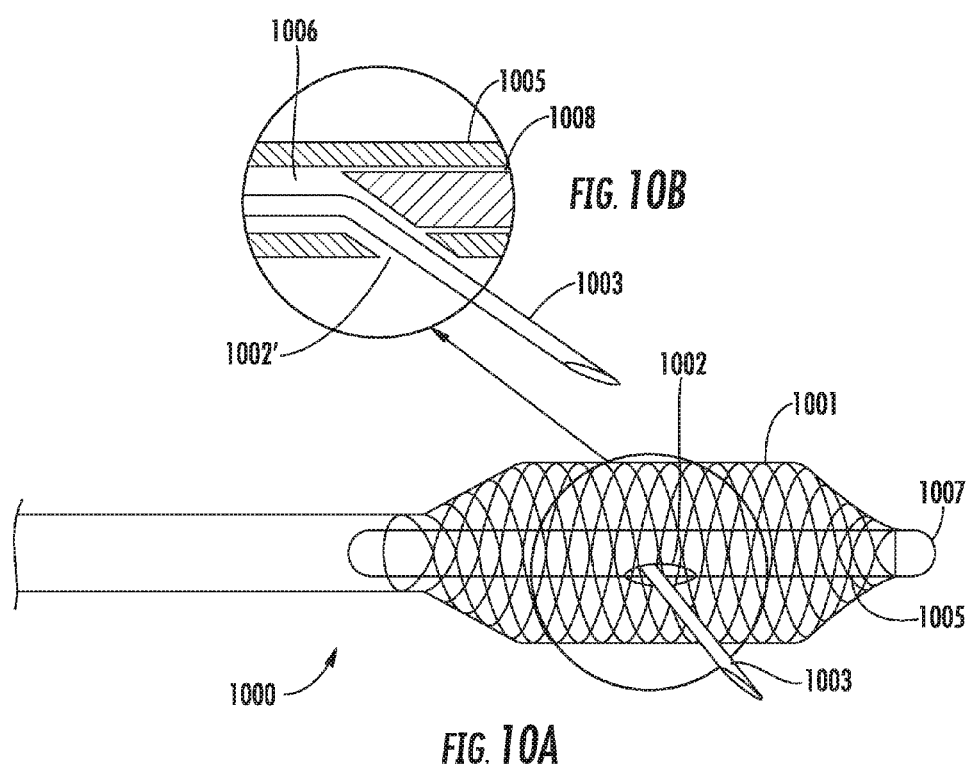

APPARATUS AND METHOD FOR PROMOTING ANGIOGENESIS IN ISCHEMIC TISSUE

CROSS-REFERENCE TO RELATED APPLICATIONS

This application is a continuation-in-part application of U.S. patent application Ser. No. 15/072,249, filed Mar. 16, 2016, the entire contents of which are incorporated herein by reference.

FIELD OF THE INVENTION

The present invention is directed to apparatus and methods for promoting tissue perfusion in the vascular territory served by vessels occluded by severe atherosclerosis by delivering biologics into a subintimal space, and/or by delivering biologics from the subintimal space into tissue surrounding the vessel.

BACKGROUND OF THE INVENTION

Peripheral arterial disease (PAD) is a highly prevalent disease affecting over 12 million people in the United States (Golomb et al., Circulation, 2006). As PAD progresses, atherosclerosis and chronic inflammation can result in markedly reduced blood flow to the legs, feet, and hands. Critical limb ischemia (CLI) is the most advanced stage of PAD, and affects more than 500,000 people annually, causing rest pain in the foot, non-healing ulcers, delayed wound healing, limb/digital gangrene, and may eventually lead to amputation.

Conventional treatment for severe arterial occlusive disease includes bypassing or crossing the occlusions using endovascular techniques such as angioplasty, atherectomy, and/or stents. However, many patients with severe, diffuse arterial occlusive disease, as is typically seen in CLI, are either not ideal candidates for an endovascular approach to percutaneous revascularization due to their significant co-morbidities (i.e. renal dysfunction, myocardial dysfunction) or significant functional or nutritional debilitation. Moreover, when arterial occlusions are extensive and severely calcified, which is the typical in CLI patients with femoropopliteal and infrapopliteal occlusive disease, interventional attempts to re-establish vessel patency to improve tissue perfusion are frequency sub-optimal or unsuccessful due to inability to traverse these complex, long arterial occlusions. Given this technical failure to re-establish tissue perfusion, amputation is frequently required as a life saving measure, resulting in long-term disability, a diminished quality of life and substantial expenditures to the health care system.

In recent years, stem cell therapies have been investigated as providing a possible adjunct or alternative for patients who are either "poor option" or "no option" candidates for a percutaneous interventional procedures due to extent of their occlusive disease. Stem cells are pluripotent cells with the ability to self-renew and differentiate. The therapeutic effect of stem cells to improve perfusion to ischemic tissues was first observed when administrating bone marrow cells into a mouse model of hind-limb ischemia. (Asahara et al., Circ. Res., 1999). In 2002, autologous bone marrow mononuclear cells were observed to exhibit therapeutic angiogenesis when being injected to a human patient with ischemic limbs due to PAD. (Tateishi-Yuyama et al., Lancet, 2002). While the cellular mechanism(s) behind the therapeutic effect of stem cells is still under investigation, current studies indicate that stem cells promote neo-vascularization by angiogenesis, vasculogenesis, arteriogenesis, or a combination of the three.

Stem cells are conventionally delivered via systemic infusion (i.e., intravenous or intra-arterial) or local injection near areas of ischemic tissue. These delivery methods have remained in use, and relatively static, for over a decade, and may significantly hamper the effectiveness of stem-cell therapy. Specifically, stem cell viability and retention rates after conventional delivery methods are extremely low, typically less than 10% of the injected number. To compensate for the cell loss, a much higher volume of stem cells is needed to elicit a therapeutic response. (Behfar, et al., Circ Cardiovasc Interv, 2013). However, simply injecting a larger number of stem cells cannot compensate for inefficient delivery modalities. Furthermore, stem cells have relatively large diameters and may occlude vessels, compromising their therapeutic effect and potentially contributing to worsening ischemic symptoms. (Perin et al., J Mol Cell Cardiol, 2008).

The suboptimal performance observed with conventional stem cell delivery modalities has multiple causes. First, stem cells differ from traditional therapeutics in that the cells are fragile and extremely sensitive to their microenvironments. Previously known delivery methods deposit the stem cells directly at the occlusion sites, where—due to ischemia, hypoxia, oxidative stress, or inflammation—the microenvironment may be harsh, and contribute to massive cell apoptosis. (Kurtz, et al., Int J Stem Cells, 2008; Li, et. al. Stem Cells, 2007). Further, the cell injection process may itself contribute to poor cell viability, as injection may cause mechanical disruption to the stem cells, e.g., barotrauma caused by fluid sheer and extreme pressure fluctuations. Moreover, in certain applications, such as delivery of stem cells to long femoropopliteal occlusions, the migration of stem cells to ischemic areas may be impeded by the long, calcified occlusions. Alternatively, such stem cells may be easily washed out of the delivery area or entrapped in organs if taken up by systemic circulation.

In view of the foregoing drawbacks of previously known stem cell delivery methods and apparatus, there exists a need for safe and efficacious administration of biologics, such as stem cells, to occluded vessels and ischemic tissue to promote angiogenesis, especially in patients with severely ischemic tissues. In particular, it would be advantageous to provide methods and apparatus for delivering stem cells to ischemic tissue that overcome previously known methods requiring massive direct injections with low migration or uptake, or delivery of stem cells into open arteries in the vicinity of an ischemic tissue, which results in low viability and wash out.

It therefore would be advantageous to provide methods and apparatus for delivering stem cell therapy to patients with severely ischemic tissues, wherein such methods and apparatus enhance cell viability and retention rates, and promote the overall therapeutic effect of stem cells.

It further would be desirable to provide apparatus and methods dedicated to deliver stem cells and other biologics to occluded vessels of a patient in a safe and efficient manner, such that the stem cells may be delivered to the vicinity of an occluded vessel in a protected manner that enhances cell viability and retention, and reduces the risk of wash-out and entry of such cells into systemic circulation.

It also would be desirable to provide apparatus and methods to deliver stem cells such that the stem cells are delivered into a protected environment with reduced mechanical disruption, thereby promoting stem cell viability.

It further would be desirable to provide apparatus and methods for delivering biologics to promote angiogenesis in ischemic tissue that provides uniform distribution of the biologics along a designated region.

It still further would be desirable to provide apparatus and methods suitable for delivering a metered amount of stem cells to the vicinity of an occluded vessel to promote angiogenesis.

SUMMARY OF THE INVENTION

In view of the aforementioned drawbacks of previously known stem cell delivery methods and apparatus, the present invention provides apparatus and methods for delivering biologics, such as stem cells, to a subintimal space of an occluded vessel of a patient body. In accordance with one aspect of the invention, a subintimal space is created between the medial and adventitial layers of an occluded vessel, which is expected to provide a more hospitable, protected microenvironment for the cells, thereby improving uptake into the surrounding ischemic tissue and reducing wash-out and the risk that such stems cells will be carried into systemic circulation.

Apparatus and methods are provided for delivering biologics therapies that advantageously are expected to reduce the amount of biologics needed to elicit a therapeutic response. Delivery of biologics, such as stem cells, into a supported subintimal space also is expected to reduce the potential for mechanical disruption to the biologics and improve cell viability. In addition, apparatus and methods in accordance with the present invention are expected to provide a more uniformed distribution of a metered amount of stem cells within a designated region, thereby reducing the required amount of biologics to be deposited and reducing procedural cost.

In accordance with one aspect of the present invention, a biologics delivery device is provided for creating and maintaining a subintimal space in an occluded blood vessel of a patient and for delivering a biologic into the subintimal space. The biologics delivery device comprises a catheter having a proximal end, a distal region having a distal end, a lumen extending there between, and a plurality of through-wall apertures distributed along the distal region. The plurality of through-wall apertures is in fluid communication with the proximal end and the lumen. The biologics delivery device preferably further comprises an expandable member disposed in the distal region, which is configured to transition between a collapsed state, suitable for insertion into the subintimal space, and an expanded state for delivery of biologics. During delivery of biologics, the expandable member is radially expanded to contact the walls of the subintimal space to support the space patent.

The biologics delivery device also may include an actuator for transitioning the expandable member between the collapsed state and the expanded state. The actuator also may retain the expandable member in the expanded state during biologics delivery. The actuator may be constructed to include a sheath configured to constrain the expandable member in the collapsed state. In some embodiments, the actuator may comprise a cuff disposed proximal or distal to and coupled to the expandable member, such that the expandable member may be expanded by pushing, pulling, twisting the cuff, or a combination of such motions.

In accordance with one aspect of the present invention, the plurality of through-wall apertures are radiused to reduce the risk of mechanical damage to the biologics during delivery. The plurality of through-wall apertures further preferably are sized to provide substantially uniform distribution of the biologics along the distal region of the biologics delivery device. In some embodiments, the diameters of the plurality of through-wall apertures may gradually increase in the proximal to distal direction. In some embodiments, the plurality of through-wall apertures are directed towards the adventitial layer.

The biologics delivery device further may comprise at least one radiopaque marker for tracking the location of the device under fluoroscopic visualization.

A method of using the biologics delivery device for promoting angiogenesis in an ischemic area of a patient also is provided, wherein the biologics delivery device is introduced into a previously created subintimal space. An expandable member disposed on the device is radially expanded to contact and support the surface of the subintimal space. While the expandable member is retained in the expanded state to support the subintimal space, the biologics are substantially uniformly distributed into the subintimal space through the plurality of through-wall apertures disposed along the distal region. In addition, a contrast agent may be administered with the delivery of the biologics, so that migration of the biologics out of the subintimal space and into the surrounding ischemic tissue may be observed under fluoroscopy.

In accordance with another aspect of the disclosure, a biologics delivery device is introduced into the subintimal space created between the medial and adventitial layers of an occluded vessel, and is configured to deposit biologics from the subintimal space to tissue surrounding the occluded vessel, such as skeletal muscle surrounding the vessels of a lower limb, thereby enhancing biologics survival and reducing the risk of systemic washout.

The biologics delivery device for delivering a biologic to tissue surrounding an occluded blood vessel of a patient includes a catheter having a proximal end, a distal region having a distal end, and a side wall defining a catheter lumen; an expandable member disposed in the distal region, which is configured to support a subintimal space in an occluded blood vessel of a patient, and to transition between a collapsed state and an expanded state; and a hollow needle having a penetration tip deployable from inside the catheter lumen to outside the catheter lumen, and into the tissue. The expandable member in the expanded state allows the flow of oxygenated blood to the occluded blood vessel.

The biologics delivery device also may include a side opening formed through the side wall and disposed on the distal region, wherein the hollow needle is deployed through the side opening. The catheter lumen also may terminate at the side opening.

The biologics delivery device further may include an actuator for transitioning the expandable member between the collapsed state and the expanded state. The actuator may further be configured to maintain the expandable member in the expanded state during the delivery of the biologic.

In accordance with another aspect of the present disclosure, the hollow needle is configured to be advanced through the expandable member in the expanded state. The hollow needle may be formed of nitinol. The expandable member may include a plurality of strands. The expandable member may also include a mesh-like structure.

In accordance with another aspect of the present disclosure, the biologics delivery device may include at least one radiopaque marker.

The biologic may include one or more hematopoietic stem cells, endothelial progenitor cells, mesenchymal stem cells, embryonic stem cells, induced pluripotent stem cells, growth factors, or any combination thereof.

A method of using the biologics delivery device for promoting angiogenesis in an ischemic area of a patient also is provided, wherein the biologics delivery device is introduced into a previously created subintimal space between an adventitial layer and an intimal layer of a vascular wall of an occluded blood vessel, the subintimal space having a surface. The distal end of the biologics delivery device is introduced into the subintimal space, the expandable member in the subintimal space is transitioned to an expanded state to contact and support the surface of the subintimal space. The penetration tip of the hollow needle is deployed from inside the catheter lumen to outside the catheter lumen, and into the tissue surrounding the occluded blood vessel. A biologic through the biologics delivery lumen extending through the hollow needle is delivered to the tissue. In addition, a contrast agent may be administered with the delivery of the biologics, so that migration of the biologics out of the subintimal space and into the surrounding ischemic tissue may be observed under fluoroscopy.

BRIEF DESCRIPTION OF THE DRAWINGS

FIG. 4A is a plan view of a plurality of through-wall apertures in accordance with the principles of the present invention; while

FIGS. 10A and 10B illustrate the distal region of a biologics delivery device constructed in accordance with another aspect of the present disclosure.

DETAILED DESCRIPTION OF THE INVENTION

Arteries and veins generally are comprised of three layers: the innermost layer called the intimal layer, the outermost layer called the adventitial layer, and the medial layer located in between the intimal and the adventitial layers. The intimal and medial layers are readily separated from the adventitial layer. For example, it is known that when attempting to pass an occlusion with a guidewire, the guidewire may sometimes inadvertently penetrate the subintimal space between the intimal and the adventitial layer. Hereinafter, in the context of this specification, the term "intimal layer" refers to the intima/media that adjoins the occluded vessel lumen, while the term "adventitial layer" refers to the outer layer of the vessel that may be separated from the intimal layer when a subintimal space is created.

Figure 1A:
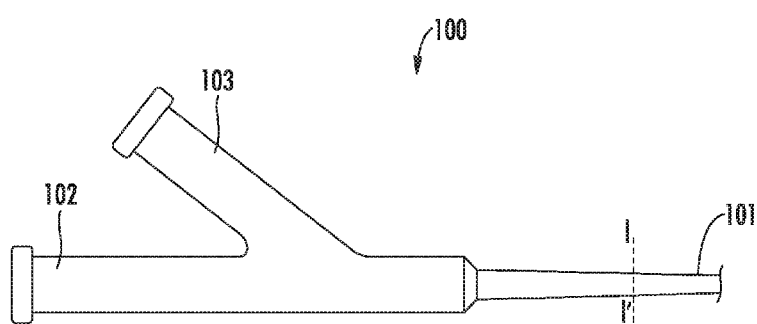
FIGS. 1A and 1B are schematic views of an illustrative biologics delivery device constructed in accordance with the principles of the present invention.
Figure 1B:
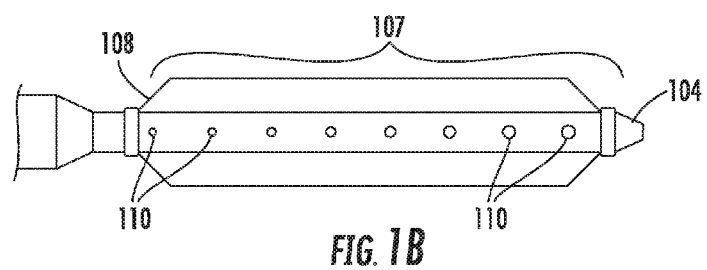

Referring to FIGS. 1A and 1B, a biologics delivery device constructed in accordance with the principles of the present invention is described. Biologics delivery device 100 comprises a catheter having an elongated catheter shaft 101 connecting proximal end 102 to distal region 107. Infusion port 103 preferably is disposed at proximal end 102 of biologics delivery device 100, and is in fluid communication with a biologics reservoir (not shown). The reservoir preferably comprises a syringe or pump for delivering a metered amount of biologics to biologics delivery device 100 through infusion port 103. Distal region 107 preferably comprises a plurality of through-wall apertures 110 disposed along the longitudinal axis of distal region 107. Distal region 107 further comprises atraumatic distal tip 104, which may include a flap or duck-bill valve to substantially prevent retrograde flow of body fluid, e.g., blood, through the lumen of biologics delivery device 100. Expandable member 108 is disposed over distal region 107, and is configured to transition between a collapsed state, suitable for insertion into the subintimal space, and an expanded state for delivery of biologics, with an increased diameter for contacting and supporting the walls to define a subintimal space of a blood vessel. Expandable member 108 may be self-expanding, wherein radially compressive force is applied to retain expandable member 108 in the collapsed state. Alternatively, expandable member 108 may be expanded by an actuator.

Biologics delivery device 100 preferably has a length and diameter suitable for use in the desired peripheral vessel, e.g., 70 cm to 150 cm in length, with a diameter from 2.5 mm to 60 mm. Distal region 107 preferably has a length of about 1 cm to 5 cm. Catheter shaft 101 may be formed of conventional materials of construction, e.g., a plastic material such as polyethylene, polyvinylchloride, polyesters or the like.

Figure 2A:
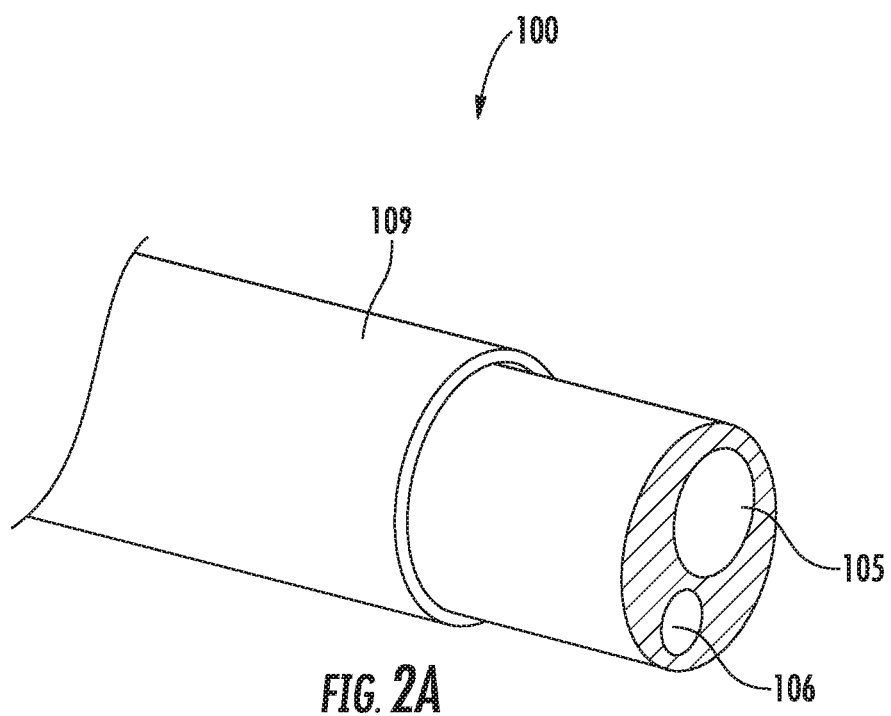
FIG. 2A is a perspective sectional view of the catheter shaft taken along line 1-1' of FIG. 1A.
Figure 2B:
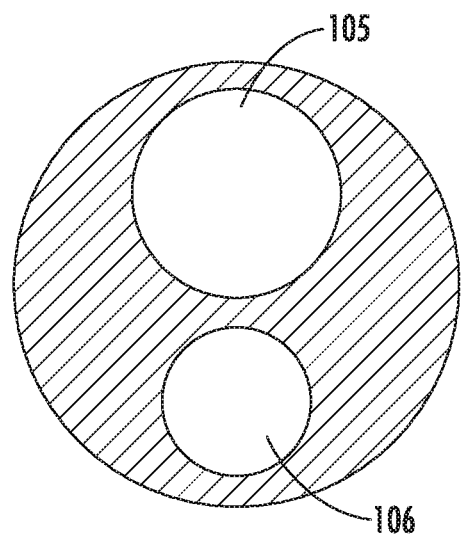
FIG. 2B is a sectional view of the catheter shaft of FIG. 2A.

FIGS. 2A to 2B illustrate perspective and end sectional views of biologics delivery device 100 taken along line 1-1' of FIG. 1A. Catheter shaft 101 comprises biologics lumen 105 and guidewire lumen 106 extending along the longitudinal axis of catheter shaft 101. Biologics lumen 105 preferably has a larger diameter than guidewire lumen 106. Biologics lumen 105 is in fluid communication with infusion port 103 at the proximal end and extends longitudinally through distal region 107, terminating at the plurality of through-wall apertures 110 of distal region 107. Guidewire lumen 106 may extend substantially parallel to biologics lumen 105, from proximal end 102 to distal tip 104. In some embodiments, guidewire lumen 106 may extend through an auxiliary port (not shown) disposed at proximal end 102. Catheter shaft 101 may be slidably disposed within sheath 109.

Figure 3A:
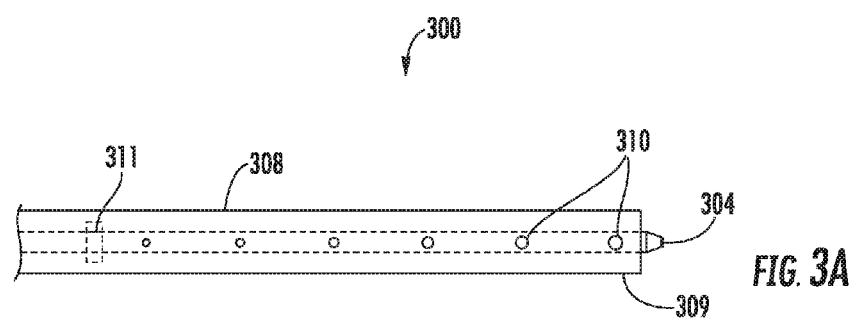
FIG. 3A is a plan view of an embodiment of the distal region of a biologics delivery device in accordance with the principles of the present invention, wherein the expandable member is in a collapsed state.
Figure 3B:
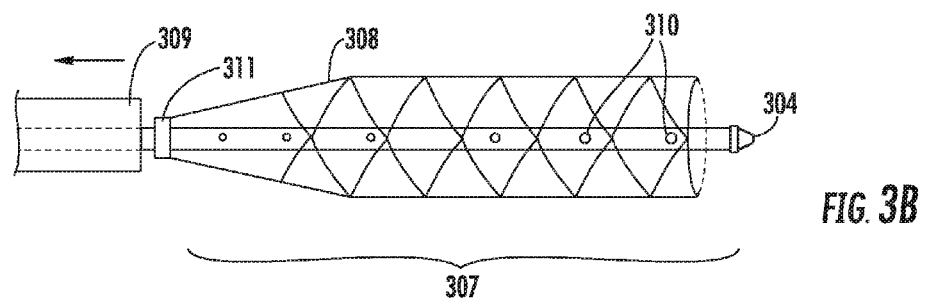
FIG. 3B is a plan view of the distal region of FIG. 3A, wherein the expandable member is in an expanded state.

Referring to FIGS. 3A to 3B, when distal region 307 of biologics delivery device 300 is located in a desired subintimal location in a vessel, expandable member 308 is radially expanded to support the subintimal space during biologics delivery. Expandable member 308 comprises a cage-like scaffold configured to transition between a collapsed state and an expanded state. The scaffold preferably comprises a mesh structure comprising a plurality of mesh cells. Expandable member 308 covers at least a portion of distal region 307, and further may comprise proximal cuff 311 coupled to distal region 307 for receiving the proximal end of the scaffold. Distal tip 304 preferably extends distally beyond expandable member 308 to assist in navigating through a blood vessel and the subintimal space.

As depicted in FIG. 3A, sheath 309 may be slidably disposed over expandable member 308 to retain expandable member 308 in a collapsed state to facilitate advancement of biologics delivery device 300 into the subintimal space along a guidewire. The guidewire (not shown) may be a conventional guidewire that is placed under fluoroscopic guidance through a patent portion of a vessel and then penetrated into the subintimal region in the vicinity of an occlusion. Biologics delivery device 300 may then be advanced along the guidewire to further separate the intimal and adventitial layers of the vessel in the region of the occlusion. After distal region 307 is located in the subintimal space and prior to biologics delivery, sheath 309 may be retracted, allowing expandable member 308 to resume its expanded configuration to enlarge and support the subintimal space, as shown in FIG. 3B. After the biologic is delivered through a plurality of through-wall apertures 310, expandable member 308 may be collapsed by re-advancing sheath 309 distally, thereby compressing expandable member 308 to its collapsed state. Expandable member 308 preferably comprises a resilient biocompatible material, such as a stainless steel or a shape-memory alloy, such as nickel titanium.

Still referring to FIGS. 3A and 3B, biologics delivery device 300 includes a plurality of through-wall apertures 310 constructed in accordance with the principles of the present invention. Apertures 310 communicate with biologics lumen 105 and may be aligned in an axial direction along the wall of catheter shaft 101, and preferably face outwards toward the adventitial layer. While FIG. 3A depicts six apertures 310 disposed in distal region 308, it should be understood that any number of apertures may be used. Apertures 310 may be of any suitable shape, for example, round, elliptical, octagonal, etc., although having a smooth circumference is generally expected to be preferred.

Figure 4A:
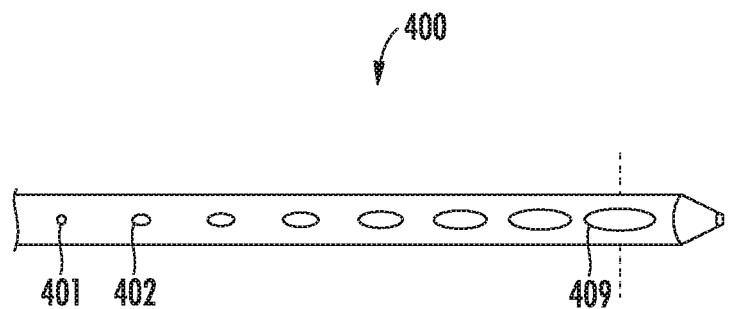
Figures 4B, 4C:
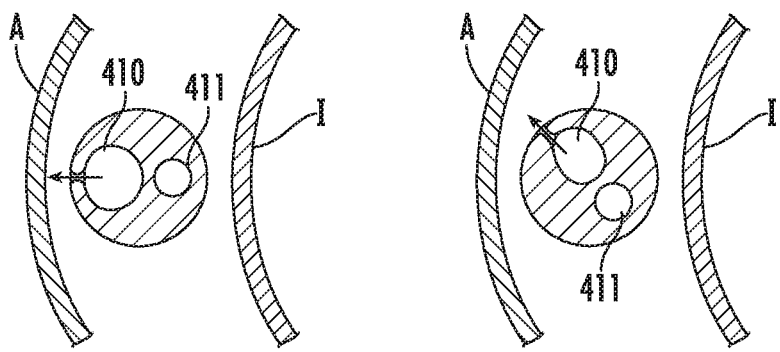
FIGS. 4B through 4D are sectional views of the plurality of through-wall apertures of FIG. 4A.
Figure 4D:
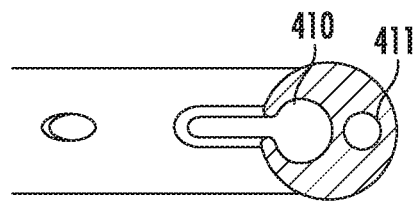

Referring now to FIGS. 4A to 4D, alternative embodiment of biologics delivery catheter 400 constructed in accordance with the principles of the present invention is described. This embodiment also includes an expandable member similar to that of the embodiment of FIGS. 3A-3B, but which is omitted in FIG. 4 for clarity. Biologics delivery catheter 400 includes a plurality of through-wall apertures, 401 to 409, constructed in accordance with the principles of the present invention. Apertures 401-409 communicate with the internal lumen of catheter 400 and preferably are oriented outwards toward adventitia A. While FIG. 4A depicts nine apertures 401-409 disposed in the distal region, it should be understood that any number of apertures may be used. The plurality of through-wall apertures 401-409 preferably gradually increase diameter or flow area in the proximal to distal direction, with the smallest apertures located nearest the proximal end of the distal region and the largest apertures located nearest the distal end of the distal region. This graded aperture design is expected to facilitate a substantially uniform distribution of biologics along the length of the distal region. In accordance with a further aspect of the present invention, apertures 401-409 preferably are radiused, as depicted in FIGS. 4B-4D, to avoid sharp edges that might cause mechanical damage to the biologics during delivery as they pass from biologics delivery lumen 410 into the subintimal space.

As for the embodiment of FIGS. 3A-3B, apertures 401-409 may be of any suitable shape, for example, round, elliptical, octagonal, etc., although having a smooth circumference is generally expected to be preferred. The apertures also may have the same or different shapes, and the space between two adjacent apertures may be uniformed or varied to assist in uniform delivery of the biologic. As will be apparent to one of ordinary skill based on the present disclosure, the diameters of the apertures may be determined by the size of the catheter and/or the volume and the size of the biologics to be delivered.

Biologics lumen 410 is disposed adjacent to guidewire lumen 411 and is in fluid communication with apertures 401-409. The size and positioning of biologics lumen 410 preferably are selected to reduce biologics residue in the catheter shaft at the conclusion of the delivery, which also permits a more accurate measurement of amount of biologics delivered. In accordance with one aspect of the present invention, it is expected that depositing a biologic such as stem cells within the subintimal space will facilitate uptake into ischemic tissue, and promote angiogenesis in the following ways: First, depositing the biologic in the subintimal space will reduce the risk that blood flow in the vessel will cause wash-out of the biologic and reduce the amount that is carried into systemic circulation. Second, the subintimal space provides a more protective environment for the biologic. Third, by depositing the biologic directly into the subintimal space, uptake of the biologic will not be impeded by the presence of thrombus or calcifications as would be the case if the biologic were to be deposited into a tunnel formed with thrombus located in the vessel. Fourth, because the biologic is delivered directly into a healthier subintimal tissue environment than if delivered within the vessel proper, the biologic is expected to be much more likely to obtain necessary nutrition from the surrounding tissue, thereby enhances survival. Fifth, because delivering the biologic into the subintimal space reduces the risk of wash-out, smaller amounts of biologic may be used than would otherwise be possible, thereby reducing the material costs of such a procedure. Sixth, a nutrient matrix may be administered in combination with the biologic into the subintimal space, thereby further improving biologic viability.

Figure 5A:
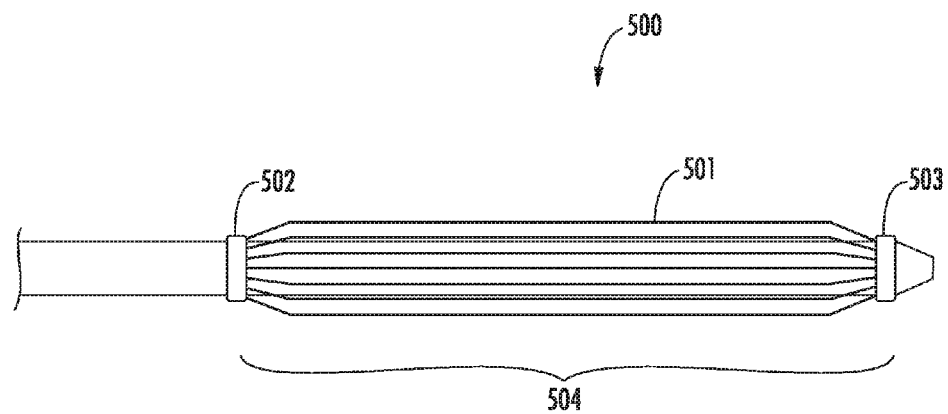
FIGS. 5A and 5B illustrate the distal region of an alternative embodiment of a biologics delivery device constructed in accordance with the principles of the present invention.
Figure 5B:
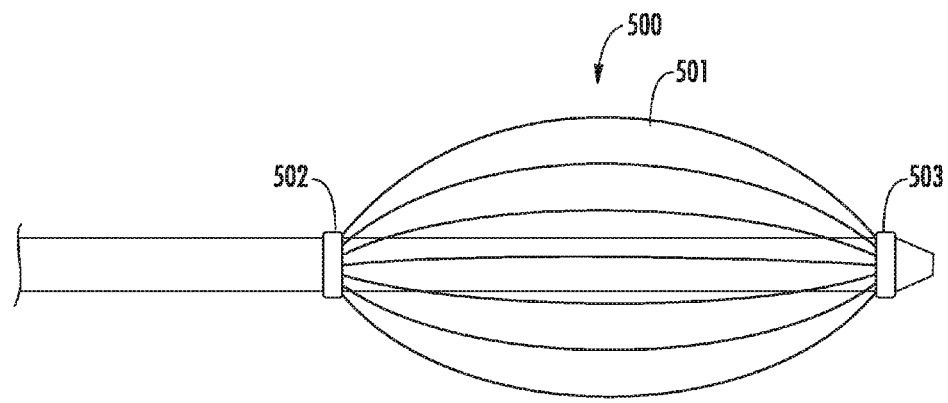

Referring to FIGS. 5A and 5B, in accordance with another embodiment, expandable member 501 comprises a plurality of elongated strands. Proximal cuff 502 is slidably disposed on distal region 504 and engages the proximal ends of the plurality of strands. Distal cuff 503 is affixed to distal region 504 and engages the distal ends of the plurality of strands. Expandable member 501 is configured to transition between a collapsed state, as shown in FIG. 5A, and an expanded state, as shown in FIG. 5B. Preferably, expandable member

501 is expanded by pushing proximal cuff 502 distally, thereby causing the plurality of strands to expand radially outwards. Alternatively, the proximal cuff may be affixed to the distal region, while the distal cuff is slidably disposed on distal region, whereby pulling distal cuff 503 proximally expands the expandable member. Expandable member 501, in the expanded state, may assume a substantially cylindrical shape having tapered proximal and distal ends. A clinician may actuate proximal cuff 502 or distal cuff 503 at the proximal end of biologics delivery device 500 using a wire, a suture, a sheath, or any other suitable method known in the art.

Figure 6A:
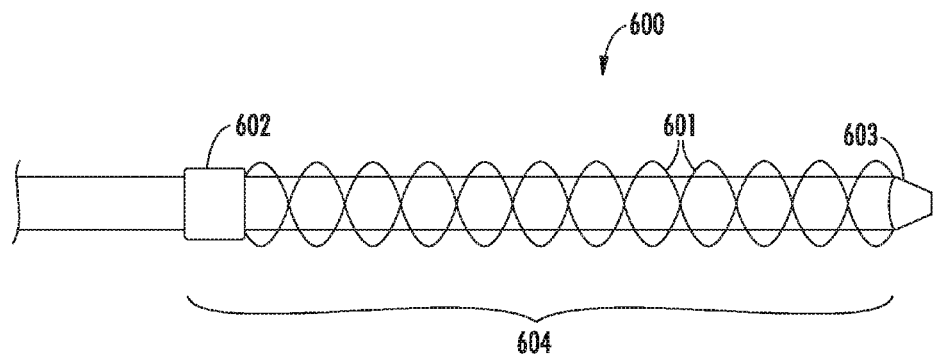
FIGS. 6A and 6B illustrate the distal region of another alternative embodiment of a biologics delivery device constructed in accordance with the principles of the present invention.
Figure 6B:
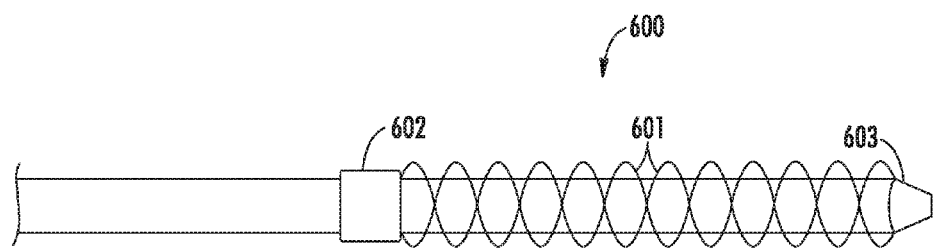

FIGS. 6A and 6B depict another alternative embodiment of an expandable member. Expandable member 601 comprises a plurality of helical strands disposed over distal region 604. Proximal cuff 602 engages the proximal ends of the plurality of strands and is slidably disposed on distal region 604, while the distal ends of the plurality helical strands are affixed to the catheter at distal end 603. Alternatively, the plurality of helical strands may be affixed to catheter at their proximal ends, and a cuff may be disposed to slide proximally over distal region 604 to engage the distal ends of the plurality of strands, thereby causing the helical strands to expand radially outward. Pulling, pushing or twisting an actuator or handle disposed at the proximal end of biologics delivery device 600 may expand expandable member 601. The number of helical strands disposed over distal region 604 may range from one to six or more, but preferably includes at least two strands 180 degrees out of phase.

Figure 7:
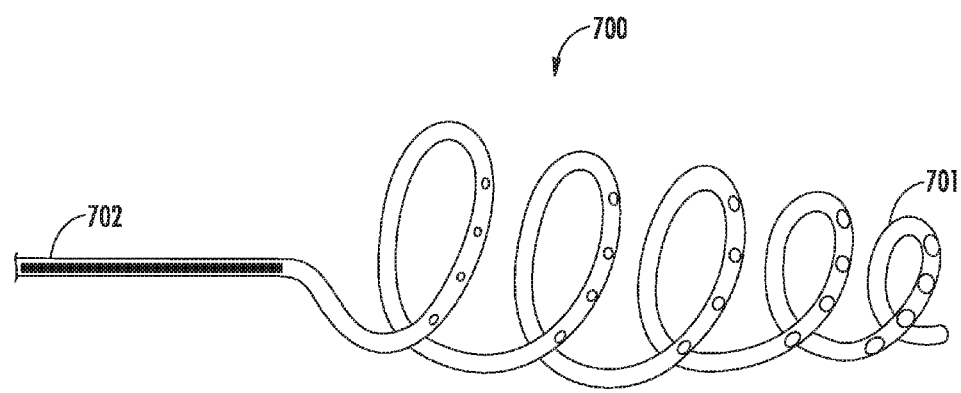
FIG. 7 is a perspective view of the distal region of yet another embodiment of a biologics delivery device in accordance with the principles of the present invention.

With respect to FIG. 7, a further alternative embodiment of biologics delivery device 700 is described, in which a distal region of biologics delivery device 700 comprises hollow coiled wire 701. The distal end of hollow coiled wire 701 may be tapered to facilitate advancement in vessel lumen. Hollow coiled wire 701 defines a lumen that is in fluid communication with a reservoir for introducing biologics into said lumen. Hollow coiled wire 701 further comprises outwardly directed plurality of through-wall apertures for delivering biologics directed towards the adventitia layer of a subintimal space. Consistent with the other embodiments and aspects of the present invention described above, the apertures of hollow coiled wire 701 may be of variable diameters and shapes for delivering a substantially uniformed distribution of biologics along the length of the coiled wire. Hollow coiled wire 701 may be made of a shape-memory alloy, such as nickel titanium. In operation, hollow coiled wire 701 is configured to be straightened and threaded along the longitudinal axis by guidewire 702 until disposed in a subintimal space. Hollow coiled wire 701 may then assume a coiled shape when guidewire 702 is retracted.

The distal region in accordance with the principles of the present invention preferably has a length of 1.0 cm to 5.0 cm and may be tapered to facilitate delivery. The expandable member may be permanently coupled to the catheter shaft or may be manufactured as a separate piece and coupled to the device prior to use.

Figure 8A:
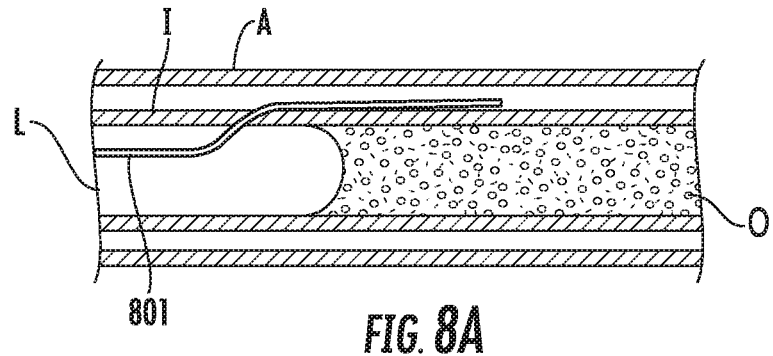
FIGS. 8A to 8C illustrate the steps of creating a subintimal space in accordance with the principles of the present invention.
Figure 8B:
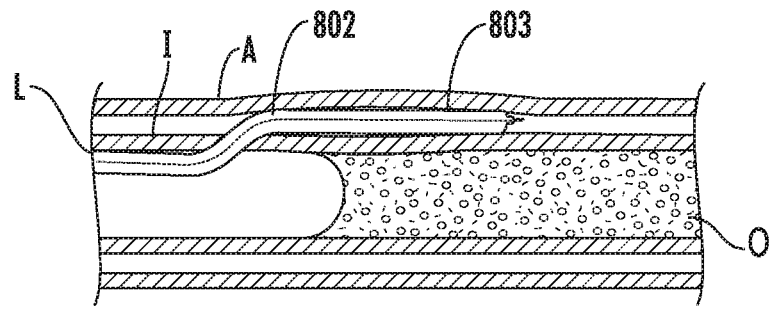
Figure 8C:
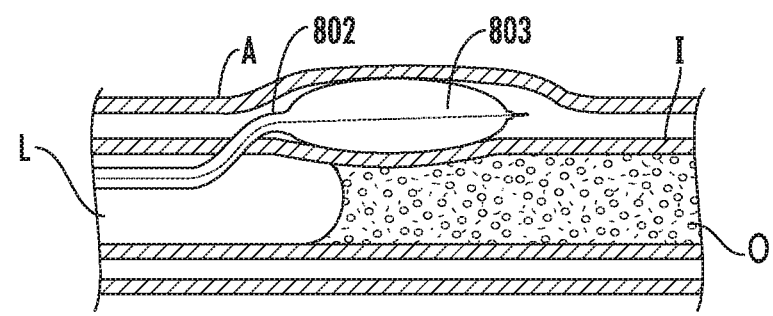

Referring to FIGS. 8A to 8C, a method of creating a subintimal space for biologics delivery in accordance with the principles of the present invention is now described. First, as depicted in FIG. 8A, guidewire 801 is advanced through vessel lumen L to a location proximate to occlusion O blocking vessel lumen L. Guidewire 801 then is advanced so that the distal tip of the guidewire penetrates through intima I into the medial layer of the vessel, as may be determined under fluoroscopic visualization. With the distal tip of guidewire 801 located between intima I and adventitia A, guidewire 801 is further advanced distally to create a subintimal space there between alongside occlusion O in the vessel. Additionally, and/or alternatively, another catheter device, such as a microcatheter comprising a distal tip to facilitate piercing and/or dissection of tissue layers of the blood vessel, may be used. If the additional catheter is used to enter the subintimal space, guidewire 801 may be re-advanced through the additional catheter and back into the subintimal space. The additional catheter then is withdrawn, leaving guidewire 801 positioned in the subintimal space, as shown in FIG. 8A.

The lumen defining the subintimal space may subsequently be dilated using a balloon angioplasty catheter, atherectomy device, by stenting, or other known techniques. As shown in FIGS. 8B and 8C, balloon catheter 802 having inflatable balloon 803 at the distal end may be introduced over guidewire 801 to dilate the subintimal space. Balloon catheter 802 may be advanced into the subintimal space in a delivery configuration, with balloon 803 deflated. Once the balloon is positioned in the vicinity of a desired position for biologics delivery, preferably distal to the proximal end of occlusion O, balloon 803 preferably is inflated to expand radially to dilate the subintimal space. Balloon 803 may then be deflated and withdrawn over guidewire 801. Additionally and/or alternatively, subintimal laser atherectomy may be performed using a laser catheter, if significant calcification or fibrosis is present. Once the subintimal space is created and supported, balloon 803 is deflated and balloon catheter 802 is withdrawn.

Figure 9:
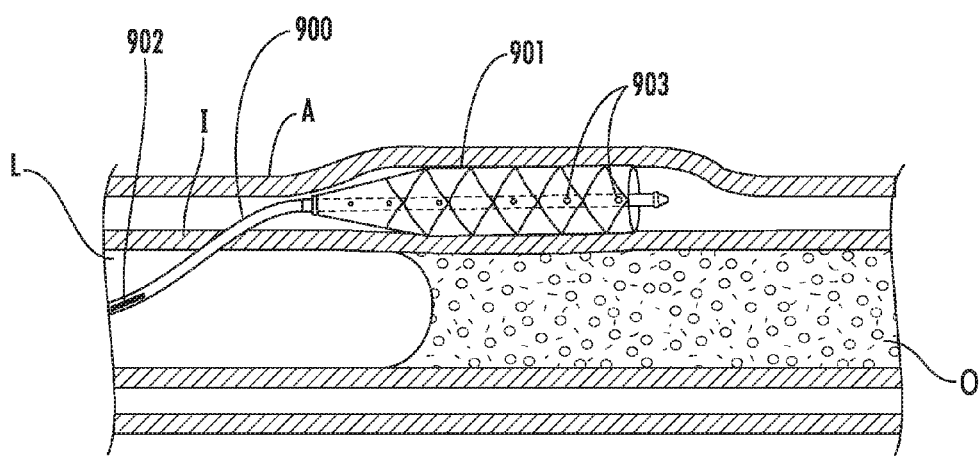
FIG. 9 illustrates delivering biologics to the subintimal space using an embodiment of a biologics delivery device in accordance with the principles of the present invention.

FIG. 9 depicts biologics delivery using the embodiment of biologics delivery device 900 similar to that described with respect to FIGS. 3A-3B. Biologics delivery device 900 is advanced into the subintimal space over guidewire 902 to a desired biologics delivery location, preferably distal to the proximal end of occlusion O. Biologics delivery device 900 is preferably pre-warmed to about the same temperature of the patient, for example, 37° C.; whereas the proximal end of device 901 may be maintained at room temperature. Expandable member 901 is introduced to the subintimal space in a collapsed state, and then is expanded radially to contact and support the walls of the subintimal space. Expandable member 901 preferably is maintained in the expanded state during biologics delivery, as shown in FIG. 9.

Biologics delivery device 900 may comprise one or more radiopaque markers to assist placement of the device under fluoroscopic visualization, and to confirm dilation of the subintimal space prior to and during biologics delivery.

A metered amount of prepared biologics solution or suspension may be infused into the biologics lumen from a reservoir and deposited towards adventitia A through a plurality of through-wall apertures 903 disposed along the distal region of biologics delivery device 900. Biologics preferably are injected in a solution or suspension, a hydrogel, or in a microsphere formulation that buffers the biologics during delivery and reduces mechanical damage. A fluid flow controller may be provided to meter fluid flow from the reservoir into the biologics lumen at a selected fluid pressure. The fluid or suspension used to deliver the biologics also may include a contrast agent to assist in visualizing delivery of the biologics into the subintimal space, and subsequent uptake into the surrounding tissue. Optionally, the biologics lumen is flushed with saline or other suitable fluid to reduce biologics residue in the biologics lumen.

The biologic may be fluorescently labeled and tracked using scintigraphy, PET, or MRI. The expandable member preferably is maintained in the expanded state for a predetermined period to facilitate migration of the stem cells into the adventitial layer before the device is re-collapsed and withdrawn. The expandable member preferably is configured to re-collapse sufficiently slowly to avoid damaging the deposited biologics.

In accordance with one aspect of the present invention, stem cells used in conjunction with the apparatus and method described herein above may be collected from a number of allogeneic and autologous sources.

A mixed population of various types of undifferentiated cells may be collected from a patient's bone marrow, including hematopoietic stem cells (HSCs), endothelial progenitor cells (EPCs), and mesenchymal stem cells (MSCs). HSCs are stem cells that form blood and immune cells and can be readily isolated from bone marrow, umbilical cord blood, or after mobilization into peripheral blood. MSCs are another type of adult bone marrow derived stem cells with the ability to form cartilage, bone, adipose tissue, and marrow stroma, and are capable of sustained expression of growth factors. MSCs also may be isolated from adipose tissue, the umbilical cord, fetal liver, muscle, and lung, and can be successfully expanded in vitro. Endothelial progenitor cells are primitive bone marrow cells that also are reported to possess the ability to mature into cells that form vessel walls. (Luttun et al., Trends Cardiovasc Med. 2002.) In addition to bone marrow stem cells, embryonic stem (ES) cells are capable of unlimited self-renewal while maintaining the potential to differentiate into almost all cell lineages. The ethical issues related to ES cells promoted the development of induced pluripotent stem (iPS) cells, which share many properties with ES cells without the ethical concerns. Additionally, the stem cells may be combined with growth factors such as EGF, FGF, GDF, IGF, PDGF, and VEGF to promote cell differentiation.

The present disclosure also provides apparatus and methods for delivering biologics, such as stem cells, from a subintimal space of an occluded vessel of a patient body to tissue surrounding the occluded vessel.

In accordance with one aspect of the present disclosure, biologics may be delivered from the subintimal space to tissue surrounding the vessel. In a non-limiting example, where the occluded vessel is located in the lower limb of a patient, tissue surrounding the occluded vessel may be skeletal muscle. Tissue surrounding the occluded arteries may receive blood supply from other vessels, and therefore may be viable and less hypoxic comparing to the occluded vessel. Depositing the biologics into such a friendlier environment is expected to enhance biologics survival, and reduce the risk of systemic washout.

Figure 10C:
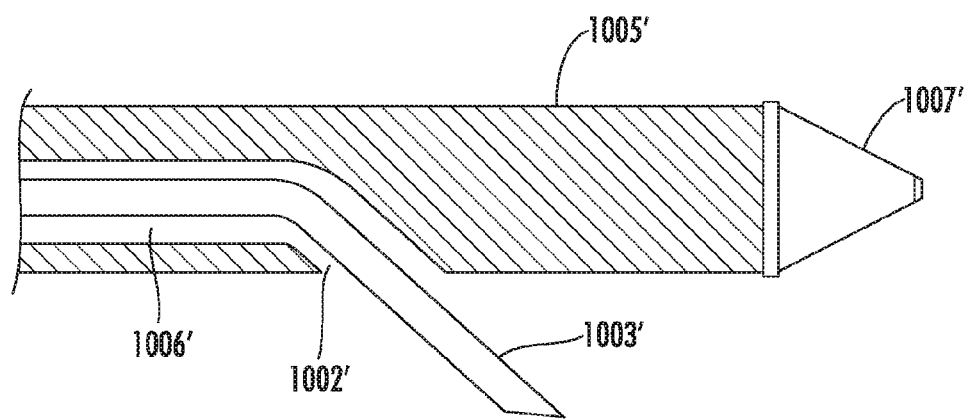
FIG. 10C illustrates an alternative embodiment of a distal region of a biologics delivery device in accordance with the principles of the present disclosure.
Figure 11:
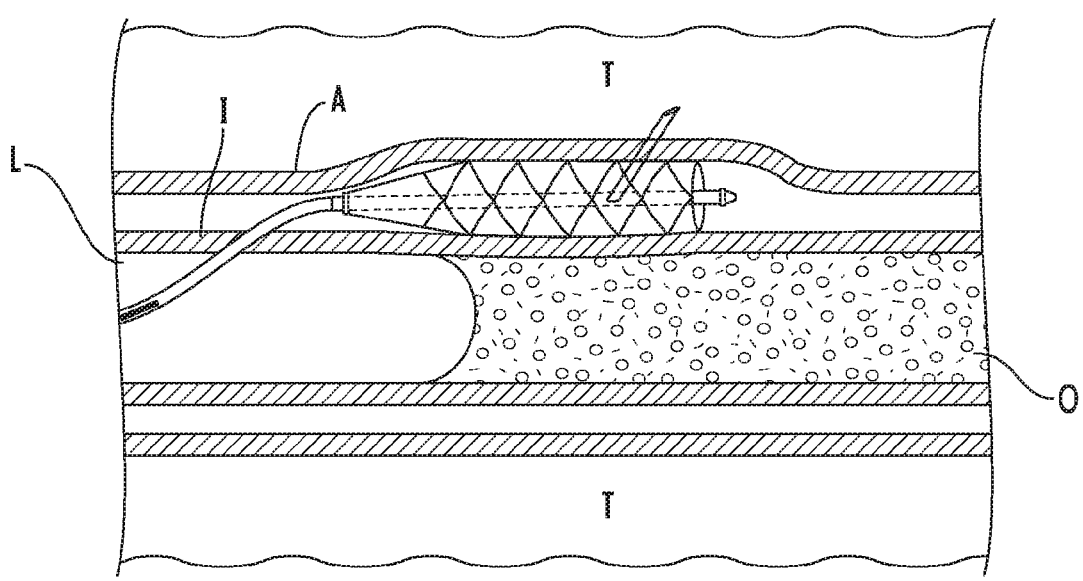
FIG. 11 illustrates delivering biologics from the subintimal space to tissue surrounding the occluded vessel using an embodiment of a biologics delivery device in accordance with the principles of the present disclosure.

Referring now to FIGS. 10A-C, alternative biologics delivery devices constructed in accordance with the principles of the present disclosure are described. The proximal parts of these embodiments are similar to that of the embodiments described in FIGS. 1A, 2A, 2B, but which are omitted in FIGS. 10A-C for clarity. Distal region 1000 preferably includes expandable member 1001 disposed over elongated catheter shaft 1005, through-wall aperture 1002 disposed on the side wall of elongated catheter shaft 1005, and needle 1003 configured to be retractably deployed from lumen 1006 of elongated catheter shaft 1005, through through-wall aperture 1002, to penetrate adventitial wall A, and into tissue T surrounding the occluded blood vessel. Tissue T may be any tissue surrounding the occluded blood vessel, for example, skeletal muscle. Expandable member 1001 as shown in FIG. 10A includes a braided structure commonly known as the "Chinese Finger Trap." Those skilled in the art will understand that expandable member 1001 may comprise any embodiments of the expandable member disclosed herein.

Still referring to FIG. 10A, needle 1003 preferably includes a biologics lumen extending therethrough. The proximal end of the biologics lumen may be in fluid communication with a reservoir of biologics. Needle 1003 preferably comprises a nitinol needle having a beveled tip, and a curved distal region configured to be retractably deployed from the sidewall of elongated catheter shaft 1005, forming an angle with the longitudinal axis of elongated catheter shaft 1005. Needle 1003 may be configured to deliver biologics into tissue T. Needle 1003 has an outer diameter that may be fit within lumen 1006, preferably from about 20 Gauge to about 30 Gauge.

Elongated catheter shaft 1005 may include additional components to facilitate the positioning and deployment of needle 1003. As seen in FIGS. 10A-B, lumen 1006 extends through elongated catheter shaft 1005, terminating at distal tip 1007. Stop 1008 may be disposed in lumen 1006 distal to through-wall aperture 1002. Alternatively, as seen in FIG. 10C, lumen 1006' may terminate at through-wall aperture 1002', without extending through elongated catheter shaft 1005' to distal tip 1007'. The distal end of needle 1003' may be flexible and deflected by a curved portion of elongated catheter shaft 1005' (not shown) protruding into lumen 1006'. The curved protrusion may be an inflation balloon.

Expandable member 1001 preferably maintains in the expanded state during delivery of the biologics, and needle 1003 preferably extends through the mesh opening of expandable member 1001. In accordance with one aspect of the present disclosure, expanding the subintimal space while delivering the biologics may allow for the introduction of oxygenated blood into the vicinity of tissue T, which is expected to further promote the viability of the deposited biologics.

In accordance with another aspect of the present disclosure, the beveled tip of needle 1300 may include at least one radiopaque marker. Additionally, elongated catheter shaft 1005 further may comprise at least one radiopaque marker. The radiopaque markers may be configured to track the location of the device, and/or deployment of needle 1003 into tissue T under fluoroscopic visualization. Additionally, and/or alternatively, the proximal end of device 1000 may include at least one fiduciary mark indicating the deployment of needle 1003.

Biologics delivery device 1000 also may include a plurality of apertures disposed on elongated catheter shaft 1005, and may be configured to deposit biologics into both the subintimal space and tissue T surrounding the occluded blood vessel.

Those skilled in the art will appreciate that the invention can be practiced in other than the described embodiments, which are presented for purposes of illustration and not of limitation.

What is claimed is:

1. A method of promoting angiogenesis in an ischemic area of a patient body, comprising:
   accessing a subintimal space between an adventitial layer and an intimal layer of a vascular wall of an occluded blood vessel, the subintimal space having a surface;
   providing a biologics delivery device comprising a catheter having a proximal end, a distal region having a distal end, a side wall defining a catheter lumen, an expandable member configured to transition between a collapsed state and an expanded state, and a retractably deployable hollow needle within the catheter lumen, the hollow needle having a penetration tip and a biologics delivery lumen extending therethrough;

introducing the distal end of the biologics delivery device into the subintimal space;

transitioning the expandable member positioned in the subintimal space to an expanded state to contact and support the surface of the subintimal space;

deploying the penetration tip of the needle from inside the catheter lumen to outside the catheter lumen, through the expandable member, and into tissue surrounding the occluded blood vessel; and delivering a biologic through the biologics delivery lumen to the tissue.

2. The method of claim 1, wherein deploying the penetration tip of the hollow needle comprises deploying the penetration tip of the hollow needle from a side opening formed through the side wall of the catheter.

3. The method of claim 1, wherein the expandable member comprises a plurality of strands, and wherein transitioning the expandable member to the expanded state comprises compressing the plurality of strands until the plurality of strands expands radially outward.

4. The method of claim 1, wherein transitioning the expandable member to the expanded state comprises retracting a sheath slidably receiving the expandable member.

5. The method of claim 1, wherein the expandable member comprises a plurality of mesh cells.

6. The method of claim 1, wherein deploying the penetration tip of the hollow needle comprises deploying the penetration tip of the hollow needle through the expandable member in the expanded state.

7. The method of claim 1, wherein deploying the penetration tip of the hollow needle comprises deploying a nitinol needle.

8. The method of claim 1, further comprising determining the deployment of the hollow needle using at least one radiopaque mark disposed on the biologics delivery device.

9. The method of claim 1, wherein the biologic comprises one or more hematopoietic stem cells, endothelial progenitor cells, mesenchymal stem cells, embryonic stem cells, induced pluripotent stem cells, growth factors, or any combination thereof.

* * * * *